United States Patent
Kumakawa et al.

[11] Patent Number: 6,134,970
[45] Date of Patent: Oct. 24, 2000

[54] CONTACT PRESSURE DETECTING SENSOR AND CONTACT PRESSURE MEASURING DEVICE INCLUDING SAME

[75] Inventors: Yoshiyuki Kumakawa, Kanagawa; Hiromi Sanada, Ishikawa, both of Japan

[73] Assignee: Cape Co., Ltd., Japan

[21] Appl. No.: 09/412,350

[22] Filed: Oct. 5, 1999

[30] Foreign Application Priority Data

Oct. 6, 1998 [JP] Japan .................................. 10-284289

[51] Int. Cl.$^7$ .............................. G01L 7/02; A61B 5/117
[52] U.S. Cl. ............................................. 73/730; 600/595
[58] Field of Search ............................. 73/730 OR, 713, 73/714, 729.1, 729.2, 756, 172; 600/592, 595, 597

[56] References Cited

U.S. PATENT DOCUMENTS

| | | | |
|---|---|---|---|
| 5,079,536 | 1/1992 | Chpman | 338/99 |
| 5,993,400 | 11/1999 | Rincoe et al. | 600/595 |

OTHER PUBLICATIONS

Kabushiki Kaisha AMI, "Contact Pressure Measuring Device for Soft Surface–Pressure Measuring Device for Clothes," brochure (Japanese), Jul. 1995.
Tally, "Oxford Pressure Monitor," leaflet (date unknown).
Roho Inc., "Therapoint," leaflet (date unknown.

*Primary Examiner*—William Oen
*Assistant Examiner*—Abdullahi Aw-Musse
*Attorney, Agent, or Firm*—Lerner, David, Littenberg, Krumholz & Mentlik, LLP

[57] ABSTRACT

A contact pressure detecting sensor having a simplified structure. The sensor includes a pair of air-impermeable sheets and at least one foamed plastic member interposedly arranged between the air-impermeable sheets while being kept from being uncompressed. The foamed plastic member is capable of resuming its original configuration after compression. The sensor also includes at least one tube arranged so as to extend from the vicinity of the foamed plastic member to outside the air-impermeable sheets. The air-impermeable sheets are joined to each other at portions thereof positioned around the foamed plastic member and tube.

12 Claims, 5 Drawing Sheets

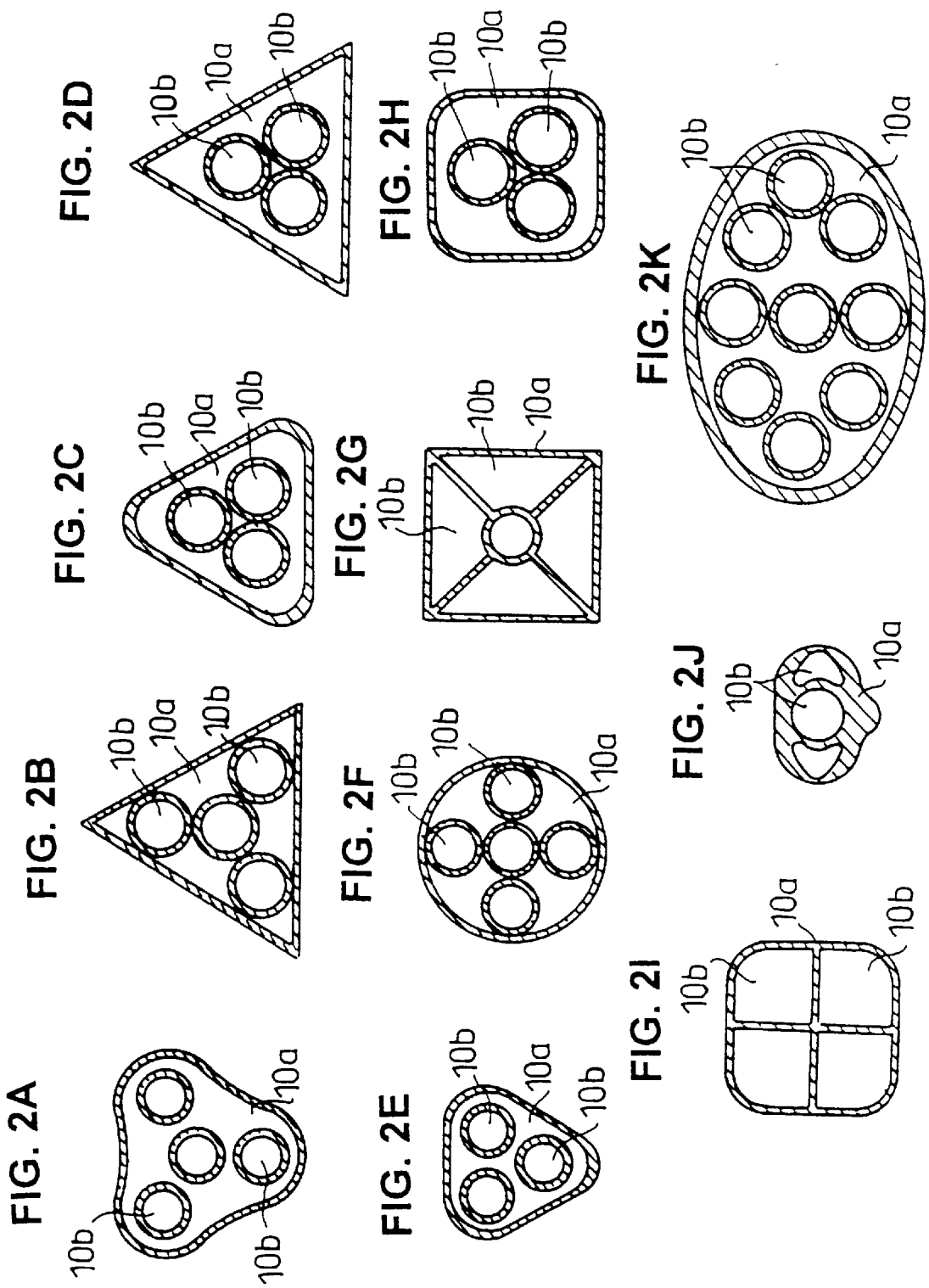

CONTACT PRESSURE DETECTING SENSOR AND CONTACT PRESSURE MEASURING DEVICE INCLUDING SAME

BACKGROUND OF THE INVENTION

This invention relates to a contact pressure detecting sensor and a contact pressure measuring device including the same, and more particularly to a contact pressure detecting sensor for measuring a contact pressure occurring between each of parts or regions of the body of a patient or the like in bed and bedding and a contact pressure measuring device having such a contact pressure detecting sensor incorporated therein.

In recent years, in a nursing or caregiving field such as a home, a hospital or the like, nursing or care for bedridden patients keeps on increasing with an increase in aged people. In such a field, patients are typically subject to continuous pressure over a long period of time, to thereby be exposed to a danger of bedsore. An idea that such pressure is reduced to prevent occurrence of the bedsore leads to commercial development of a variety of bedsore prevention instruments such as an air mattress and the like in the world.

Separately from such an approach as described above, a variety of contact pressure measuring devices have been developed which are adapted to measure a magnitude of a pressure actually applied to each of parts of the body of a patient. One of the contact pressure measuring devices is constructed so as to arrange a number of sensors all over a bed, so that signals outputted from the sensors are analyzed through a computer to display a pressure distribution while classifying the pressures by color. Such a contact pressure measuring device is typically used for researches and made to order, resulting in being highly expensive and large-sized. Also, operation of the contact pressure measuring device requires high-grade knowledge and skill.

Thus, currently it is substantially impossible in an actual nursing or caregiving field to detailedly know conditions which cause a surface of the body of a patient in bed to be subject to pressure, as well as a degree of improvement in a pressure environment by employment of a bedsore preventing equipment. Therefore, nursing or caregiving staff substantially fails to know a danger of occurrence of bedsore in a patient due to a pressure which is inherently unobservable, leading to occurrence or worsening of bedsore which would be able to be necessarily prevented.

Recently, a relatively small-sized contact pressure measuring device unlike the large-sized device described above is developed. The small-sized contact pressure measuring device includes such a contact pressure sensor as indicated at reference numeral 40 in FIGS. 5A and 5B. The contact pressure sensor 40 is so constructed that two films 40a are laminated on each other so as to define a hollow section 40b therebetween and a tube 40c is arranged in a manner to be drawn out of the hollow section 40b. Then, a coupler 40d is mounted on a distal end of the tube 40c.

In operation of the contact pressure sensor 40 thus constructed, a predetermined amount of air is injected into the hollow section 40b. Injection of air is carried out through the coupler 40d provided therein with a check valve (not shown) by means of an exclusive or dedicated air cylinder (not shown). Thus, the check valve prevents air in the hollow section 40b from leaking out of the hollow section 40b after the air cylinder is detached from the sensor 40 following injection of air. Then, the coupler 40d is fitted in a socket of a body of the contact pressure measuring device. This permits opening of the check valve of the coupler 40d, so that a pressure of air in the hollow section 40b of the contact pressure sensor 40 may be applied to a pressure detector arranged in the body of the measuring device. A pressure applied to the pressure detector is varied depending on a pressure applied to the contact pressure sensor 40, so that a signal outputted from the pressure detector is subjected to electrical processing for display.

Unfortunately, in the conventional contact pressure measuring device, operation of injecting air into the hollow section 40b by the air cylinder is highly troublesome. Also, the air cylinder and the coupler of the contact pressure sensor are complicated in structure, to thereby fail to reduce the cost. Such complication of the structure often leads to further disadvantages such as leakage of air and the like.

SUMMARY OF THE INVENTION

The present invention has been made in view of the foregoing disadvantages of the prior art.

Accordingly, it is an object of the present invention to provide a contact pressure detecting sensor which has a simplified structure.

It is another object of the present invention to provide a contact pressure measuring device which includes such a contact pressure detecting sensor and is capable of readily measuring a magnitude of pressure occurring between a surface of the body of a patient and bedding.

In accordance with one aspect of the present invention, a contact pressure detecting sensor is provided. The contact pressure detecting sensor includes a pair of air-impermeable sheets and at least one foamed plastic member interposedly arranged between the air-impermeable sheets while being kept uncompressed. The foamed plastic member is capable of resuming its original configuration after compression. The contact pressure detecting sensor also includes at least one tube arranged so as to extend from the vicinity of the foamed plastic member to outside the air-impermeable sheets. The air-impermeable sheets are joined to each other at portions thereof positioned around the foamed plastic member and tube.

In a preferred embodiment of the present invention, the foamed plastic member may be made of one of a foamed polyurethane resin material and a foamed polyethylene resin material and formed to have a thickness of 1 to 3 mm.

Also, in a preferred embodiment of the present invention, the air-impermeable sheets may each be made of one of a polyurethane film and a vinyl chloride film and formed to have a thickness of 0.02 to 0.3 mm.

Further, in a preferred embodiment of the present invention, a plurality of the foamed plastic members are arranged and a plurality of the tubes are arranged, the number of the plurality of the foamed plastic members corresponding to the number of the plurality of the tubes.

In the contact pressure detecting sensor thus constructed, application of a pressure to the contact pressure detecting sensor causes the foamed plastic member to be compressed, resulting in air contained in the foamed plastic member being outwardly forcedly discharged through the distal end of the tube. When the foamed plastic member is released from the pressure applied thereto, it is permitted to return to the original state, to thereby suck air through the distal end of the tube thereinto, resulting in returning to the original configuration. Thus, it will be noted that the contact pressure detecting sensor per se exhibits a self-inflatable function. This permits the contact pressure detecting sensor to be portable while being kept separated from a body of a contact pressure measuring device and eliminates a necessity of arranging any specific instrument or means for injecting a predetermined amount of air into the sensor, so that the sensor may be connected to the body of the contact pressure measuring device at any desired time in a nursing or caregiving field.

In accordance with another aspect of the present invention, a contact pressure measuring device is provided. The contact pressure measuring device includes a contact pressure detecting sensor constructed as described above, as well as a pressure detector coupled to a distal end of the tube of the contact pressure detecting sensor so as to generate a pressure signal and a conversion circuit arranged so as to receive the pressure signal of the pressure detector. The conversion circuit outputs a converted output signal in such a manner that the conversion circuit outputs a converted output signal corresponding to the pressure signal without subjecting the pressure signal to any processing when the pressure signal fed from the pressure detector is a single signal and that the conversion circuit outputs a converted output signal corresponding to either an average value of the pressure signal or a maximum value thereof when the pressure signal fed from the pressure detector is a plurality of signals. The contact pressure measuring device also includes a display section for displaying the converted output signal of the conversion circuit in a digitized form.

In the contact pressure measuring device thus constructed, when a pressure is applied to the contact pressure detecting sensor while keeping the sensor connected to the contact pressure measuring device, air in the sensor forces the pressure detector through the distal end of the tube. Such forcing or compression permits the pressure detector to output a voltage depending on a gauge pressure based on the compression. The outputted voltage is subjected to amplification and conversion into a digital electric signal in such a manner as widely known in the art, followed by outputting to the conversion circuit. The conversion circuit functions to output a converted output signal corresponding to the pressure signal without subjecting the pressure signal to any processing when the pressure signal is a single signal and to output a converted output signal corresponding to either an average value of the pressure signal or a maximum value thereof when the pressure signal is a plurality of signals. Then, the converted output signal is displayed in a digitized form on the display section.

The conversion circuit is provided with a change-over switch so that either the average value or the maximum value may be suitably selected. For example, a part of the body of bedridden patient which is highly pressed by bedding is a sacral vertebra or the like, which is predominantly subject to bedsore. Thus, when a contact pressure on the part is to be measured, a maximum value of the plurality of signals is employed. Whereas when a pressure on the whole body is to be measured, the average value is employed.

The contact pressure measuring device is thus constructed in a simplified manner, to thereby be rendered portable, resulting in effectively preventing not only occurrence of bedsore but worsening of bedsore which has already occurred.

BRIEF DESCRIPTION OF THE DRAWINGS

These and other objects and many of the attendant advantages of the present invention will be readily appreciated as the same becomes better understood by reference to the following detailed description when considered in connection with the accompanying drawings; wherein:

FIGS. 2A to 2K each are a schematic plan view showing an essential part of another embodiment of a pressure contact detecting sensor according to the present invention;

DETAILED DESCRIPTION OF THE PREFERRED EMBODIMENTS

Now, the present invention will be described hereinafter with reference to FIGS. 1A to 4.

Figure 1A:
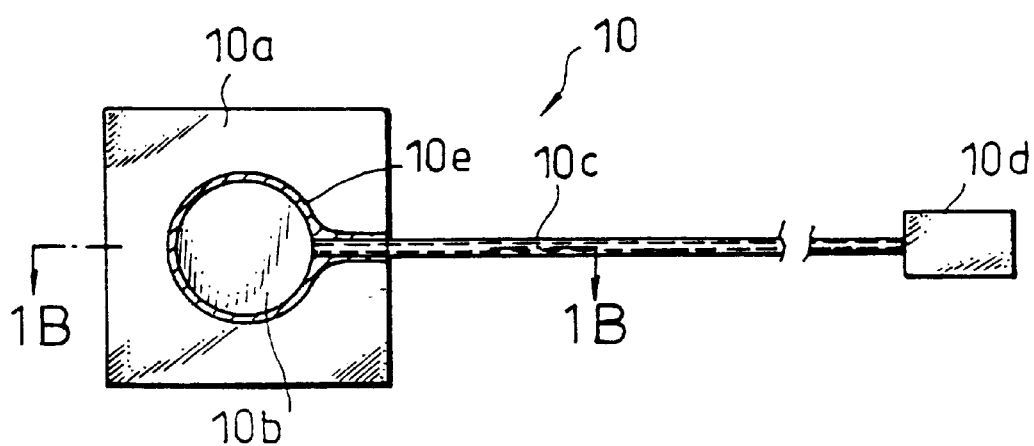
FIG. 1A is a plan view showing an embodiment of a contact pressure detecting sensor according to the present invention.
Figure 1B:
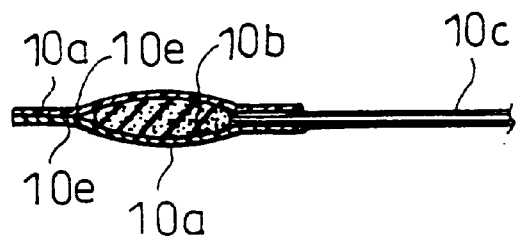
FIG. 1B is a sectional view taken along line 1B—1B of FIG. 1A.

Referring first to FIGS. 1A and 1B, an embodiment of a contact pressure detecting sensor according to the present invention is illustrated. A contact pressure detecting sensor of the illustrated embodiment which is generally designated at reference numeral 10 includes a pair of air-impermeable sheets 10*a* of 0.3 mm in thickness and a foamed plastic member 10*b* interposedly arranged between the air-impermeable sheets 10*a* while being kept uncompressed therebetween. The foamed plastic member 10*b* is formed to have a diameter of 25 mm and a thickness of 2 mm and capable of resuming its original configuration after compression. The contact pressure detecting sensor of the illustrated embodiment also includes a tube 10*c* arranged so as to extend from the vicinity of the foamed plastic member 10*b* to outside the air-impermeable sheets 10*a*. The tube 10*c* is mounted on a distal end thereof with a coupler 10*d*, which is constructed so as to be fitted in or inserted into a socket 22 provided in a body 20 of a contact pressure measuring device shown in FIGS. 3A to 3C. The air-impermeable sheets 10*a* arranged opposite to each other are jointed to each other at portions 10*e* thereof positioned around the foamed plastic member 10*b* and tube 10*c* by high-frequency welding.

The air-impermeable sheets 10*a* may each be made of a polyurethane film, vinyl chloride film, or the like and formed to have a thickness of 0.02 to 0.5 mm. The foamed plastic member 10*b* may be made of foamed polyurethane resin, foamed polyethylene resin, or the like and formed to have a diameter of 20 to 30 mm and a thickness of 1 to 3 mm. Also, the tube 10*c* may be made of a pressure-resistant polyurethane tube material of about 1 mm in outer diameter.

Now, the manner of operation of the contact pressure detecting sensor 10 of the illustrated embodiment thus constructed will be described. When a pressure is applied to the contact pressure detecting sensor 10, the foamed plastic member 10*b* is compressed, so that air in the foamed plastic member 10*b* is forcedly outwardly discharged through the distal end of the tube 10*c*. Also, when the foamed plastic member 10*b* is released from a pressure applied thereto, it is permitted to return to the original state, so that air is sucked through the distal end of the tube 10*c* thereinto, resulting in the foamed plastic member 10b being expanded or inflated to the original configuration. Thus, it will be noted that the contact pressure detecting sensor 10 of the illustrated embodiment exhibits a self-inflatable function. This permits the contact pressure detecting sensor 10 to be rendered portable while being separated from the body 20 of the contact pressure measuring device. Also, the above-described construction of the contact pressure detecting sensor 10 eliminates a necessity of arranging any means for injecting a predetermined amount of air into the sensor 10. Thus, the contact pressure detecting sensor 10 may be connected to the body of the contact pressure measuring device for measurement of a contact pressure at any desired time in situ.

Referring now to each of FIGS. 2A to 2K, another embodiment of a contact pressure detecting sensor according to the present invention is illustrated. Reference numerals in FIGS. 2A to 2K like those in FIG. 1 designate corresponding parts. A tube or tubes 10c and a coupler 10d are omitted from FIGS. 2A to 2K for the sake of brevity. A contact pressure detecting sensor of each of the embodiments includes a plurality of foamed plastic members 10b independent from each other, resulting in being constructed so as to have a plurality of sensor elements incorporated therein.

The following description will be made in connection with the contact pressure detecting sensor shown in FIG. 2B which is of the normal or standard type, wherein air-impermeable sheets 10a are each formed to have a triangular outer configuration and four such foamed plastic members 10b are arranged between the air-impermeable sheets 10a.

Figure 3A:
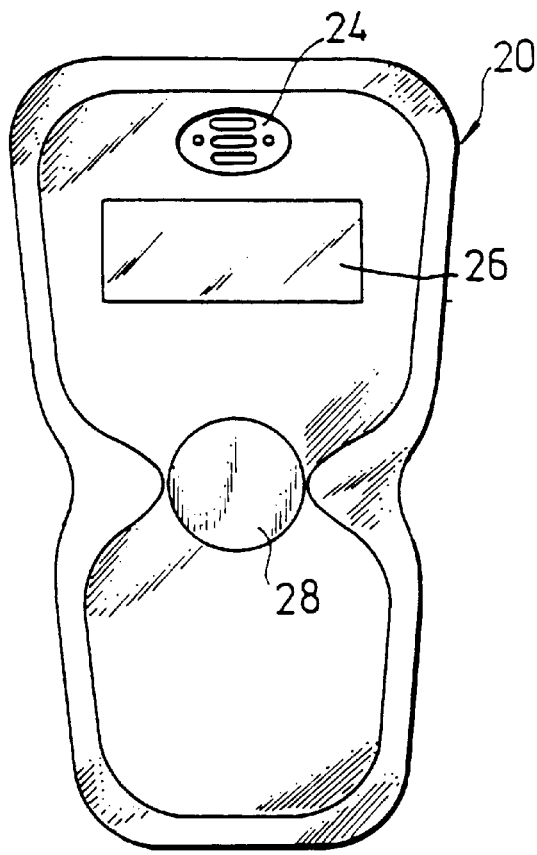
FIG. 3A is a plan view showing a body of a contact pressure measuring device according to the present invention.
Figure 3B:
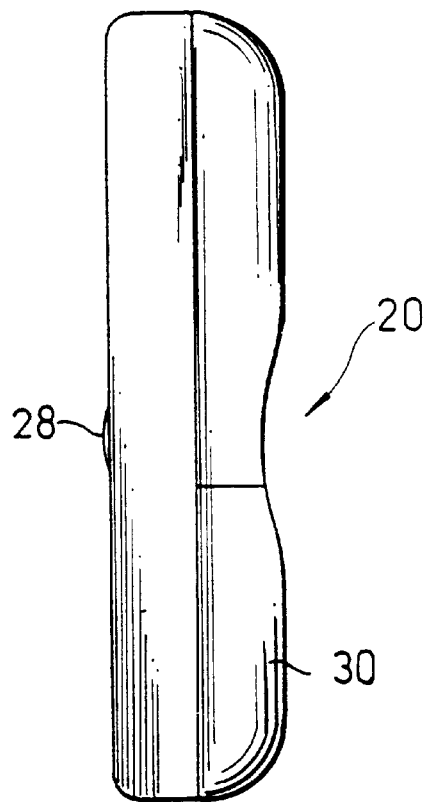
FIGS. 3B and 3C are a side elevation view of the body of the contact pressure measuring device shown in FIG. 3A and a bottom view thereof, respectively.
Figure 3C:
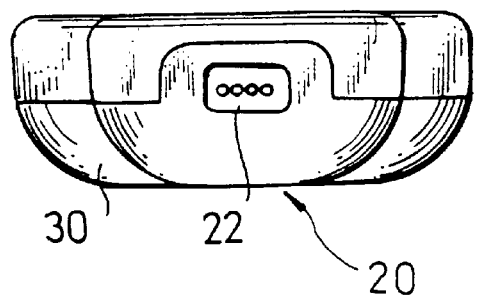

FIGS. 3A to 3C show a body 20 of a contact pressure measuring device to which the contact pressure detecting sensor 10 shown in FIG. 2B is connected. The device body 20 is formed to have a substantially parallelopiped shape having dimensions of about 140 mm in longitudinal length, about 80 mm in lateral length and about 30 mm in height. The body 20 is constricted at a central portion thereof, resulting in being readily held. The body 20 is provided on an upper portion of an upper surface thereof with a lamp 24, which is adapted to be lighted when a power supply is turned on. The body 20 is also provided on the upper surface thereof with a liquid crystal display section 26 in a manner to be positioned below the lamp 24. Further, the body 20 is provided on a central portion of the upper surface thereof with a power switch 28 for operating the power supply. In addition, the device body 20 is provided on a rear surface thereof with a lid 30, which is rendered open when mounting or dismounting of a battery with respect to the body 20 is carried out. Moreover, the body 20 is provided on a side surface thereof at one end or lower end thereof in FIG. 3A with a socket 22, in which the coupler 10d of the contact pressure detecting sensor 10 is fitted.

Figure 4:
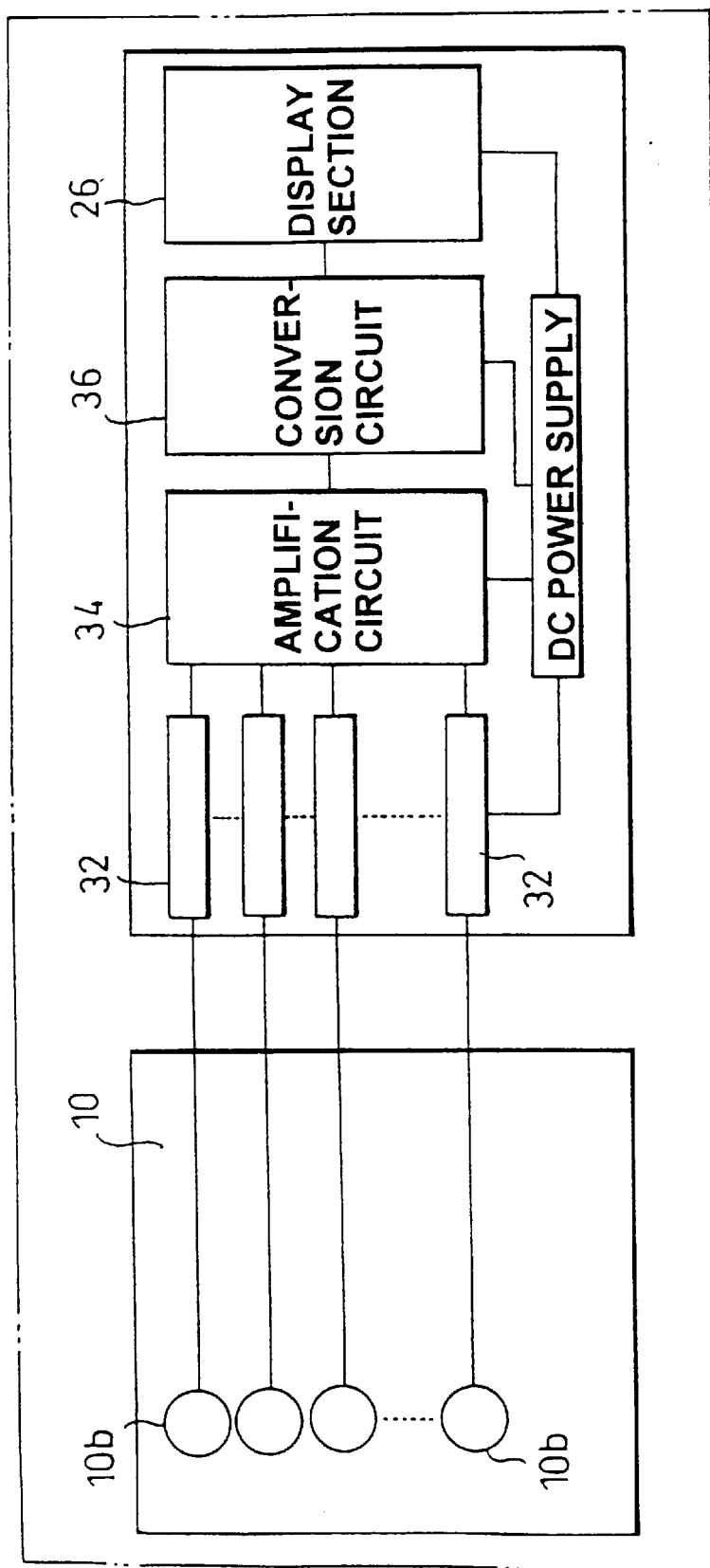
FIG. 4 is a block diagram showing a circuit for the contact pressure measuring device shown in FIG. 3A.
Figure 5A:
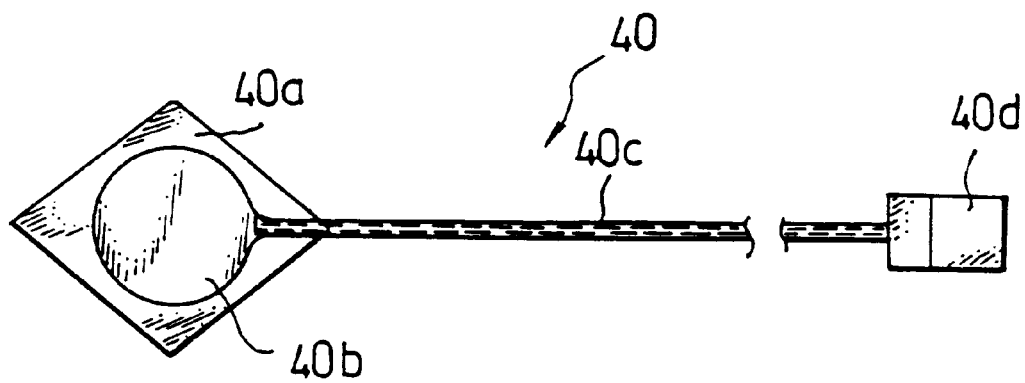
FIGS. 5A and 5B are a plan view and a side elevation view in section each showing a conventional contact pressure detecting sensor, respectively.
Figure 5B:
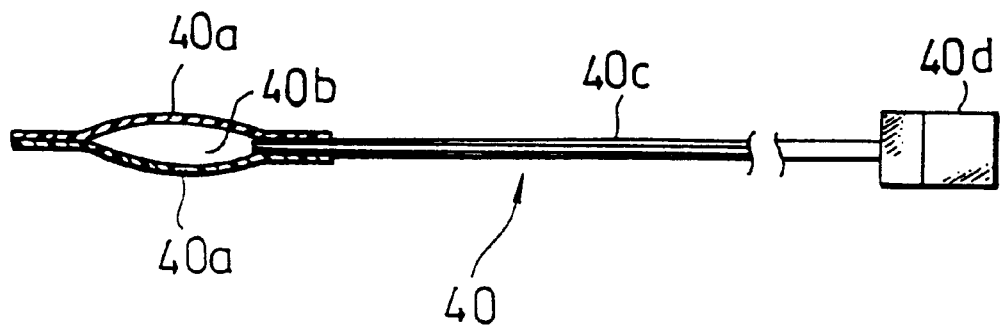

The body 20 of the contact pressure measuring device thus constructed has a circuit arranged therein, which is constructed as shown in FIG. 4. The circuit is incorporated in a circuit board, which is mounted thereon with a plurality of silicon pressure sensor elements 32 each of which corresponds to a pressure detector in the present invention. The number of the silicon pressure sensor elements 32 corresponds to the number of the foamed plastic members 10b arranged in the contact pressure detecting sensor 10. The silicon pressure sensors 32 are each connected through the socket 22 and tube 10c to the foamed plastic member 10b corresponding thereto, resulting in a gauge pressure which is a difference between an air pressure in the space in which the foamed plastic member 10b is disposed and an atmospheric pressure being converted into a voltage and outputted.

A signal thus outputted from each of the silicon pressure sensor elements 32 is amplified through an amplification circuit 34 and then inputted to a conversion circuit 36. The conversion circuit 36 first subjects the signal inputted thereto to A/D conversion. Then, when the input signal is a single signal, the conversion circuit 36 outputs a converted output signal corresponding to the input signal without subjecting the input signal to any processing, whereas when the input signal is a plurality of signals, the conversion circuit 36 outputs a converted output signal corresponding to either an average value of the input signal or a maximum value thereof. The outputted signal is then digitally displayed in a mmHg unit on the liquid crystal display section 26. Selection between the average value and the maximum value is carried out by means of a change-over switch (not shown) mounted on the circuit board. The conversion circuit is provided therein with a calibration and correction circuit for carrying out zero correction on the assumption that the foamed plastic members 10b in the contact pressure detecting sensor 10 and the silicon pressure sensors 32 are often different in characteristics.

In the contact pressure measuring device constructed as described above, the contact pressure detecting sensor 10 is arranged at a place wherein a contact pressure is to be measured such as, for example, a position of the body of a bedridden patient at which bedsore possibly occurs and then the power supply is turned on, so that a pressure applied to the sensor 10 is displayed in the form of a numerical value. A dangerous line which causes bedsore is estimated to be 32 mmHg, therefore, it is estimated that when the contact pressure applied is at a level of 32 mmHg or more, it will be required to take any desired step such as a change of a mattress into a desired one. This permits occurrence of bedsore to be previously prevented and prevents worsening of bedsore.

As can be seen from the foregoing, the contact pressure detecting sensor of the present invention is constructed to have a self-air suction or self-inflatable structure by interposing at least one foamed plastic member between the air-impermeable sheets. Such construction eliminates a necessity of arrangement of any specific instrument or means for injecting a predetermined amount of air into the sensor, to thereby permit the sensor to be connected to the body of the contact pressure measuring device at any desired time in a nursing or caregiving field. Also, it facilitates operation of the contact pressure detecting sensor and reduces a cost thereof.

Further, the contact pressure measuring device of the present invention permits measurement of pressure applied to a surface of the body of a patient from bedding to be suitably carried out with ease and at any desired time. Thus, the contact pressure measuring device effectively prevents not only occurrence of bedsore but worsing of bedsore which has already occurred.

While preferred embodiments of the invention have been described with a certain degree of particularity with reference to the drawings, obvious modifications and variations are possible in light of the above teachings. It is therefore to be understood that within the scope of the appended claims, the invention may be practiced otherwise than as specifically described.

What is claimed is:

1. A contact pressure detecting sensor comprising:

a pair of air-impermeable sheets;

at least one foamed plastic member capable of resuming its original configuration after compression and interposedly arranged between said air-impermeable sheets while being kept uncompressed; and at least one tube arranged so as to extend from the vicinity of said foamed plastic member to outside said air-impermeable sheets;

said air-impermeable sheets being joined to each other at portions thereof positioned around said foamed plastic member and tube.

2. A contact pressure detecting sensor as defined in claim 1, wherein said foamed plastic member is made of one of a foamed polyurethane resin material and a foamed polyethylene resin material and formed to have a thickness of 1 to 3 mm.

3. A contact pressure detecting sensor as defined in claim 1, wherein said air-impermeable sheets are each made of one of a polyurethane film and a vinyl chloride film and formed to have a thickness of 0.02 to 0.3 mm.

4. A contact pressure detecting sensor as defined in claim 1, wherein a plurality of the foamed plastic members are arranged and a plurality of the tubes are arranged, the number of said plurality of the foamed plastic members corresponding to the number of said plurality of the tubes.

5. A contact pressure detecting sensor as defined in claim 2, wherein a plurality of the foamed plastic members are arranged and a plurality of the tubes are arranged, the number of said plurality of the foamed plastic members corresponding to the number of said plurality of the tubes.

6. A contact pressure detecting sensor as defined in claim 3, wherein a plurality of the foamed plastic members are arranged and a plurality of the tubes are arranged, the number of said plurality of the foamed plastic members corresponding to the number of said plurality of the tubes.

7. A contact pressure measuring device comprising:

a contact pressure detecting sensor including a pair of air-impermeable sheets, at least one foamed plastic member capable of resuming its original configuration after compression and interposedly arranged between said air-impermeable sheets while being kept uncompressed, and at least one tube arranged so as to extend from the vicinity of said foamed plastic member to outside said air-impermeable sheets, said air-impermeable sheets being joined to each other at portions thereof positioned around said foamed plastic member and tube;

a pressure detector coupled to a distal end of said tube of said contact pressure detecting sensor so as to generate a pressure signal;

a conversion circuit arranged so as to receive the pressure signal of said pressure detector and output a converted output signal in such a manner that said conversion circuit outputs a converted output signal corresponding to the pressure signal without subjecting the pressure signal to any processing when the pressure signal fed from said pressure detector is a single signal and that said conversion circuit outputs a converted output signal corresponding to either an average value of the pressure signal or a maximum value thereof when the pressure signal fed from said pressure detector is a plurality of signals; and a display section for displaying the converted output signal of said conversion circuit in a digitized form.

8. A contact pressure measuring device as defined in claim 7, wherein said foamed plastic member is made of one of a foamed polyurethane resin material and a foamed polyethylene resin material and formed to have a thickness of 1 to 3 mm.

9. A contact pressure measuring device as defined in claim 7, wherein said air-impermeable sheets are each made of one of a polyurethane film and a vinyl chloride film and formed to have a thickness of 0.02 to 0.3 mm.

10. A contact pressure measuring device as defined in claim 7, wherein a plurality of the foamed plastic members are arranged and a plurality of the tubes are arranged, the number of said plurality of the foamed plastic members corresponding to the number of said plurality of the tubes.

11. A contact pressure measuring device as defined in claim 8, wherein a plurality of the foamed plastic members are arranged and a plurality of the tubes are arranged, the number of said plurality of the foamed plastic members corresponding to the number of said plurality of the tubes.

12. A contact pressure measuring device as defined in claim 9, wherein a plurality of the foamed plastic members are arranged and a plurality of the tubes are arranged, the number of said plurality of the foamed plastic members corresponding to the number of said plurality of the tubes.

* * * * *

UNITED STATES PATENT AND TRADEMARK OFFICE
CERTIFICATE OF CORRECTION

PATENT NO. : 6,134,970
DATED : October 24, 2000
INVENTOR(S) : Kumakawa *et al.*

It is certified that error appears in the above-identified patent and that said Letters Patent is hereby corrected as shown below:

Column 6, line 13, replace "mmI Ig" with --mmHg--.

Signed and Sealed this

First Day of May, 2001

*Attest:*

NICHOLAS P. GODICI

*Attesting Officer*     *Acting Director of the United States Patent and Trademark Office*